July 11, 1967 W. E. LAMMERTS Plant Pat. 2,751
ROSE PLANT
Filed June 24, 1966
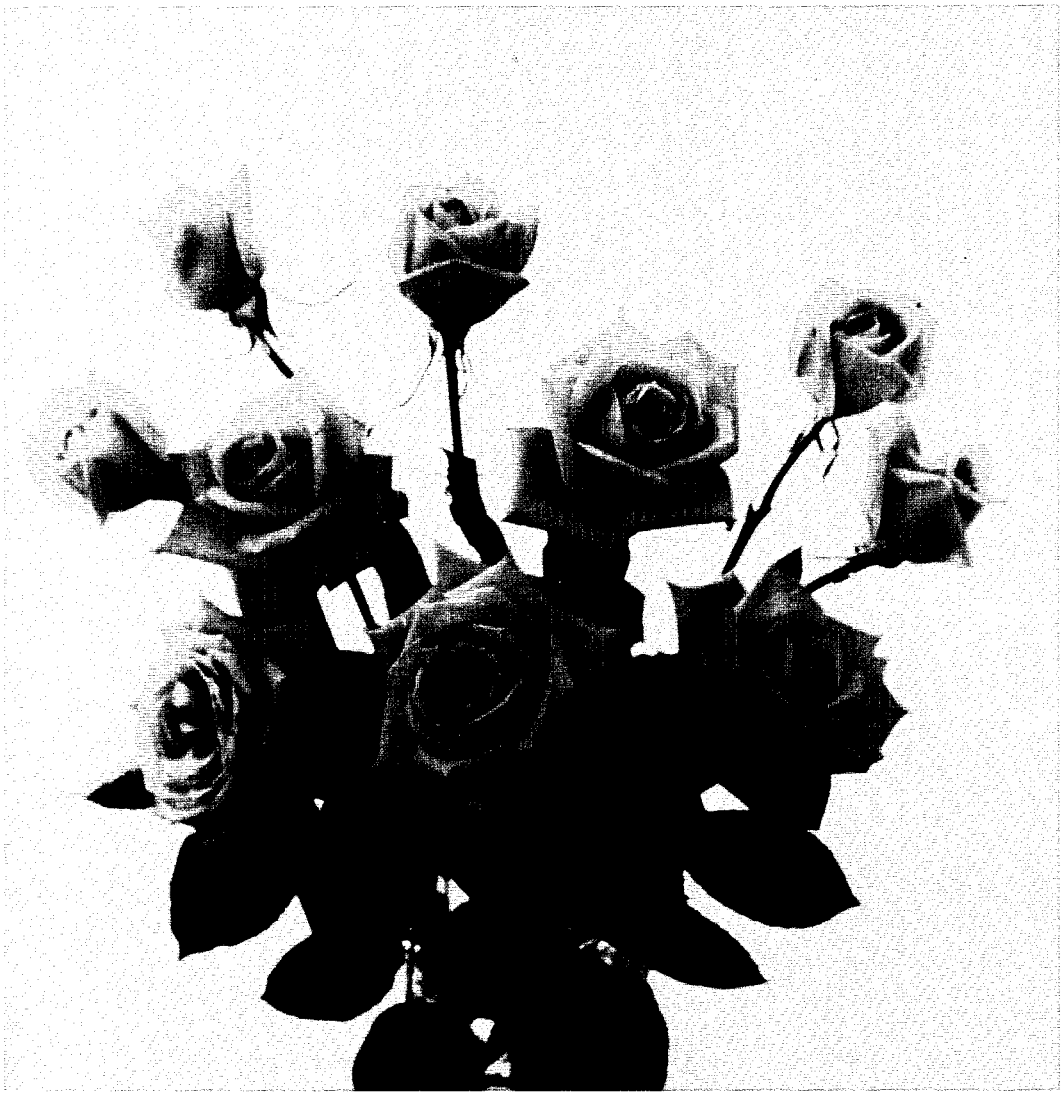
INVENTOR
WALTER E. LAMMERTS
BY Rummler & Snow
Att'ys.

United States Patent Office

Plant Pat. 2,751
Patented July 11, 1967

2,751
ROSE PLANT

Walter E. Lammerts, Freedom, Calif., assignor to Amling-Devor Nurseries, Inc., Livermore, Calif., a corporation of California

Filed June 24, 1966, Ser. No. 560,394
1 Claim. (Cl. Plt.—20)

This disclosure concerns a new and distinct variety of hybrid tea rose plant developed by me as a result of breeding efforts performed in nursery grounds at Livermore, California, since 1958. The objective sought from the said breeding efforts was to produce an unfading, non-blueing red hybrid tea rose especially suitable for greenhouse forcing and possessing improved petal substance and lasting quality of the flower, longer stems, high winter production, and rapid cycling of the flowering periods.

This new variety of rose plant originated as a seedling resulting from a cross of Baccara (Plant Pat. 1,367), as the seed parent, and Yuletide (Plant Pat. 1,391) as the pollen parent and this particular plant was discovered by me at the aforesaid nursery grounds in 1960 and at that time selected for observation and propagation. Successive asexually produced generations of this new variety have demonstrated that the plant fulfills the aforesaid objectives, and more, as will be apparent from the following detailed description, and that the improved characteristics are fixed and hold true from generation to generation.

Asexual propagation of this new variety of rose plant was first done with buds, under my direction, at Livermore, Calif. in 1961, and such propagation has been carried on continuously at Livermore since that date. Present propagation, by budding, is also done at Hamilton City, Calif. and at Phoenix, Ariz.

My new variety of rose plant is illustrated in the accompanying full color drawing which shows typical specimen of buds and flowers in several stages of opening; and the following is a detailed description of the new variety with color designations according to the Horticultural Color Chart of the British Color Council.

*The plant*

Origin: Seedling.
Parentage:
*Seed parent.*—"Baccara" (Plant Pat. 1,367).
*Pollen parent.*—"Yuletide" (Plant Pat. 1,391).
Classification:
*Botanic.*—Rosa x odorata.
*Commercial.*—Hybrid tea.
Form: Shrub.
Growth: Upright, with moderate vigor.
Branching: Upright.
Strength: Sturdy and strong.
Foliage:
*Quantity.*—Moderate—6 to 8 leaves per shoot.
*Size of leaf.*—5 to 6 inches x 3½ to 4 inches.
*Shape.*—Pinnate, with 3 to 5 leaflets.
*Leaflets.*—Ovoid, 1½ to 2½ inches long x 1¼ to 2 inches wide—coarsely serrated.
*Texture.*—Leathery and glossy.
*Color.*—Mature leaf: upper side.—Spinach Green 0960/1; under side.—Willow Green 000862/1, overlain lightly with Garnet Lake 828/3. Young leaf: upper side.—Light Spinach Green heavily overlain with Chrysanthemum Crimson 826/2; under side.—Lighter, with less green and more red.
*Ribs and veins.*—Prominent, under side.
*Petioles.*—1¼ to 1¾ inches long.
*Rachis.*—1½ to 2½ inches long.
The plant has relatively few thorns, spines and prickles.

*Color of thorns.*—Reddish when young, tan when old.
*Size of thorns.*—About ¼ inch x 5/16 inch.

*Bud*

Form: Globular—ovoid, lengthening at anthesis.
Size: 1¼" long x ¾" wide to 1½" long x 1" wide. Opens slowly—3 days from unfurling to full bloom.
Color: When sepals first divide—Cardinal Red 822.
Sepals: Curl back towards peduncle.
Hypanthium: Shape—urceolate. Size—medium; ⅜" wide x ½" long. Aspect—smooth; does not split.
Peduncle: Erect, stout and smooth. Length—2¾" to 3". Color—green.

*Flower*

Blooming habit: Recurrent, blooming profusely at 40 to 50 day intervals.
Size: Medium—3½" to 4½" diameter, 2" to 2½" depth.
Borne: Usually singly—occasional clusters of up to 3 blossoms.
Shape: High centered when bloom opens and shape does not change.
Petalage: 45 to 50 petals, obovate in form and mucronate, terminating in a short, downwardly turned claw 1/16" long. Petals are in imbricate arrangement.
*Color.*—Fresh bloom—inner and outer petals: upper side—Cardinal Red 822/2 overlain Blood Red 820/1; reverse side—Cardinal Red 822/3; petal base—small yellow-ivory eye. Old bloom: outer petals—Current Red 821/2 overlain Garnet Lake 828/2—both sides of petal; inner petals—Magenta Rose 027 on upper side and 027/1 on reverse side.
Petaloids: 18 to 22 in number—½" to 1" long, ¼" to ¾" wide. Color same as petals.
Texture: Leathery. Appearance—shiny and velvety.
Discoloration: Magenta, after full bloom.
Peduncle: 2¾" to 3" long; upright and very sturdy with ⅛" to 3/16" diameter. Color—green.
Stem: Strong, averaging over 18 inches long.
Fregrance: Moderate damask—fruity.
Lasting quality: 10 to 12 days on plant; 7 to 8 days as cut flower.
Persistence: Petals hang on and dry.
Disease resistance: Moderate for mildew, rust and blackspot as observed in growing fields at Livermore, Calif. and Phoenix, Ariz.

*Genital organs*

Stamens:
*Anthers.*—65 to 75, circularly arranged and 5/16" long, becoming longer at anthesis.
*Filaments.*—¼" long and of red color.
Pollen: Yellow in color.
Pistils: 75 to 90 in number, ¼" long, ⅜" long at anthesis.
Stigmas: Ivory in color.
Ovaries: Of ordinary character.

*Fruit*

The fruit is round in shape, fertile and of orange color at maturity.

My above described new variety of rose plant resembles Happiness (Plant Pat. 911) in flower color and form of bud; and Pink Delight (unpatented, originated by Kordes and formerly known as "Vierlanden") in habit of growth. Its distinctive characteristics and novelty reside in the brightness, richness and fidelity of the color of its blooms; the substance of its petals; the extraordinary long life of the flower both on the plant and as a cut flower; and the ability of the plant to recycle its blooming quickly during the winter months, as at Christmas and again for Valentine's Day. The long, strong stems are of a particular advantage for the cut flowers in that they possess the extraordinary capability of a very rapid uptake of water after shipping. Also, the new variety has a better bud form than Baccara or Yuletide, and has a color that is distinct from either.

Although close in color, my new variety is distinguished from Happiness by a relative freedom from thorns, by its more abundant and distinctive foliage than Happiness, and by its better keeping qualities which on vase-life tests show an average of two days longer than Happiness under comparable conditions. Also, the new variety is particularly distinguished from Happiness by its better winter production, which is a characteristic inherited from its pollen parent, Yuletide.

Having thus shown and described my new variety of rose plant, I claim:

A new and distinct variety of hybrid tea rose plant, substantially as herein shown and described, distinguished by its high winter production as a hothouse plant and its ability to recycle its flowering periods at 40 to 50 day intervals, its strong, long stems that average more than 18 inches in length, the rapid uptake of water by the cut stems after shipping, the long life of the flower on the plant and when cut, and the deep non-fading red color of its buds and blooms.

No references cited.

ABRAHAM G. STONE, *Primary Examiner.*

ROBERT E. BAGWILL, *Examiner.*